(12) United States Patent
Leclerc et al.

(10) Patent No.: US 8,409,797 B2
(45) Date of Patent: Apr. 2, 2013

(54) OPTICAL SENSORS BASED ON HYBRID APTAMER/CONJUGATED POLYMER COMPLEXES

(75) Inventors: Mario Leclerc, Québec (CA); Hoang-Anh Ho, Sainte-Foy (CA); Maurice Boissinot, Saint-Augustin-de-Desmaures (CA)

(73) Assignees: Geneohm Sciences Canada, Inc., Sainte-Foy (CA); Universite Laval, Quebec (CA)

( * ) Notice: Subject to any disclaimer, the term of this patent is extended or adjusted under 35 U.S.C. 154(b) by 633 days.

(21) Appl. No.: 10/559,098

(22) PCT Filed: Jun. 3, 2004

(86) PCT No.: PCT/CA2004/000824
§ 371 (c)(1),
(2), (4) Date: Jan. 10, 2007

(87) PCT Pub. No.: WO2004/106544
PCT Pub. Date: Dec. 9, 2004

(65) Prior Publication Data
US 2007/0196825 A1 Aug. 23, 2007

Related U.S. Application Data

(60) Provisional application No. 60/474,950, filed on Jun. 3, 2003.

(30) Foreign Application Priority Data

Jun. 3, 2003 (CA) .................................... 2430910

(51) Int. Cl.
*C12Q 1/68* (2006.01)
(52) U.S. Cl. .......................................... 435/6.1; 536/24.5
(58) Field of Classification Search .................... None
See application file for complete search history.

(56) References Cited

U.S. PATENT DOCUMENTS
5,631,146 A 5/1997 Szostak et al.

FOREIGN PATENT DOCUMENTS
WO WO 02/081735 A2 10/2002

OTHER PUBLICATIONS

Tuerk, C. and L. Gold (1990). Systematic Evolution of Ligands by Exponential Enrichment: RNA Ligands to Bacteriophage T4 DNA Polymerase. Science, v.249:505-510.*
Gold, L. (1995) Oligonucleotides as Research, Diagnostic, and Therapeutic Agents. J. of Biol. Chem., v.270(23):13581-4.*
Michaud, et al. (2004) Immobilized DNA Aptamers as Target-Specific Chiral Stationary Phases for Resolution of Nucleoside and Amino Acid Derivative Enantiomers. Analytical Chemistry, v.76(4):1015-20.*
Bock, et al., Selection of single-stranded DNA molecules that bind and inhibit human thrombin, *Nature* 355:564-566 (1992).
Ewbank, et al., Amine functionalized polythiophenes: synthesis and formation of chiral, . . . , *Tetrahedron Letters* 42:155-157 (2001).
Ho, et al., Colorimetric and Fluorometric Detection of Nucleic Acids Using Cationic . . . , *Angew. Chem. Int.* 41(9):1548-1551 (2002).
Ho, et al., New Colorimetric and Fluorometric Chemosensor Based on a Cationic . . . , *J. Am. Chem. Soc.* 125:4412-4413 (2003).
Ho, et al., Optical Sensors Based on Hybrid Aptamer/Conjugated Polymer Complexes, *J. Am. Chem. Soc.* 126:1384-1387 (2004).
Bäuerle, The synthesis of Oligothiophenes, Chapter 3, *Handbook of Oligo- and Polythiophenes*, D. Fichou Ed., Wiley-VCH, Weinheim, pp. 89-181 (1999).
Basu et al., Direct detection of monovalent metal ion binding to a DNA G-quartet by 205T1NMR. *J. Am. Chem. Soc.* 122:3240-1 (2000).
Bernier et al., A versatile approach to affinitychromic polythiophenes, *J. Am. Chem. Soc.* 124(42):12463-8 (2002).
Blank et al., Systematic evolution of a DNA aptamer binding to rat brain tumor microvessels: Selective targeting of endothelial regulatory protein pigpen, *J Biol Chem.* 276(19):16464-8 (2001).
Chen et al., Highly sensitive biological and chemical sensors based on reversible fluorescence quenching in a conjugated polymer, *Proc. Natl. Acad. Sci. U.S.A.* 96(22):12287-92 (1999).
Clark et al., Aptamers as analytical reagents, *Electrophoresis* 23(9):1335-40 (2002).
Davis et al., Use of a high affinity DNA ligand in flow cytometry, *Nucleic Acids Res.* 24(4):702-6 (1996).
Drolet et al., An enzyme-linked oligonucleotide assay, *Nature Biotechnol.* 14(8):1021-5 (1996).
Ellington et al., In vitro selection of RNA molecules that bind specific ligands, *Nature* 346:818-22 (1990).
Faïd et al., Responsive supramolecular polythiophene assemblies. *J. Am. Chem. Soc.* 120(2):5274-8 (1998).
Fan et al., High-efficiency fluorescence quenching of conjugated polymers by proteins, *J. Am. Chem. Soc.* 124(20):5642-3 (2002).
Fan et al., Photoluminescence quenching of water-soluble conjugated polymers by viologen derivatives: Effect of hydrophobicity, *Langmuir* 19(8):3554-6 (2003).
Famulok et al., Nucleic acid aptamers—from selection in vitro to applications in vivo, *Acc Chem Res.* 33(9):591-9 (2000).
Gaylord et al., DNA hybridization detection with water-soluble conjugated polymers and chromophore-labeled single-stranded DNA, *J. Am. Chem. Soc.* 125(4):896-900 (2003).
Green et al., Aptamers as reagents for high-throughput screening, *Biotechniques* 30(5):1094-1010 (2001).
Hamaguchi et al., Aptamer beacons for the direct detection of proteins, *Anal. Biochem.* 294(2):126-31 (2001).

(Continued)

*Primary Examiner* — Jennifer McDonald
(74) *Attorney, Agent, or Firm* — Knobbe Martens Olson & Bear LLP

(57) ABSTRACT

An optical sensor for detecting a target comprising a singlestranded aptamer complementary to said target, and a water-soluble cationic polythiophene derivative of the following formula: wherein "n" is an integer ranging from 6 to 100, is disclosed. The optical sensor allows for the detection of targets selected from the group consisting of potassium ions, small organic molecules, amino acids, proteins, whole cells and nucleotides. The detection is based on the formation of hybrid anionic aptamer/cationic poly-thiophene complexes.

26 Claims, 7 Drawing Sheets

OTHER PUBLICATIONS

Leclerc, M., Optical and electrochemical transducers based on functionalized conjugated polymers, *Adv. Mater.* 11(18):1491-8 (1999).

Lee et al., A fiber-optic microarray biosensor using aptamers as receptors, *Anal. Biochem.* 282(1):142-6 (2000).

Li et al., Molecular aptamer beacons for real-time protein recognition, *Biochem. Biophys. Res. Commun.* 292(1):31-40 (2002).

Lin et al., High-affinity and specific recognition of human thyroid stimulating hormone (hTSH) by in vitro selected 2'-amino-modified RNA, *Nucleic Acids Res.* 24(17):3407-14 (1996).

Liss et al., An aptamer-based quartz crystal protein biosensor, *Anal. Chem.* 74(17):4488-95 (2002).

McQuade et al., Conjugated polymer-based chemical sensors, *Chem. Rev.* 100(7):2537-74 (2000).

Michaud et al., Immobilized DNA aptamers as target-specific chiral stationary phases for resolution of nucleoside and amino acid derivative enantiomers, *Anal. Chem.* 76:1015-1020 (2004).

Nilsson et al., Conformational transitions of a free amino-acid-functionalized polythiophene induced by different buffer systems, *J. Phys. Condens. Matter* 14:10011-10020 (2002).

O'Sullivan, C.K., Aptasensors—the future of biosensing?, *Anal. Bioanal. Chem.* 372:44-48 (2002).

Padmanabhan et al, The structure of α-Thrombin inhibited by a 15-mer single-stranded DNA aptamer, *J. Biol. Chem.* 268(24):17651-4 (1993).

Robertson et al., Selection in vitro of an RNA enzyme that specifically cleaves single-stranded DNA, *Nature* 344(6265):467-8 (1990).

Tuerk et al., Systematic evolution of ligands by exponential enrichment: RNA ligands to bacteriophage T4 DNA polymerase, *Science* 249:505-10 (1990).

Ueyama et al., A novel potassium sensing in aqueous media with a synthetic oligonucleotide derivative. Fluorescence resonance energy transfer associated with Guanine quartet-potassium ion complex formation, *J. Am. Chem. Soc.* 124(48):14286-7 (2002).

Wang et al., A DNA aptamer which binds to and inhibits thrombin exhibits a new structural motif for DNA, *Biochemistry* 32(8):1899-904 (1993).

International Search Report and Written Opinion dated Jan. 31, 2005 from PCT/CA04/00824.

International Preliminary Patentability Search dated Dec. 8, 2005 from PCT/CA04/00824.

Kankia et al., Folding of the Thrombin Aptamer into a G-Quadruplex with Sr: Stability, Heat, and Hydration, J Am Chem Soc., (2001) 123(44): 10799-10804.

Michaud et al., A DNA Aptamer as a New Target-Specific Chiral Selector for HPLC, J Am Chem Soc., (2003) 125(28): 8672-8679.

Nutiu et al., Structure-Switching Signaling Aptamers, J Am Chem Soc., (2003) 125(16): 4771-4778.

Osborne et al., Nucleic Acid Selection and the Challenge of Combinatorial Chemistry, Chem Rev., (1997) 97(2): 349-370.

Vairamani et al., GQuadruplex Formation of Thrombin-Binding Aptamer Detected by Electrospray Ionization Mass Spectrometry, J Am Chem Soc., (2003) 125(1): 42-43.

European Office Communication dated Jun. 17, 2008 in EP Application No. 04737768.4, filed Jun. 3, 2004.

European Office Communication dated Apr. 23, 2009 in EP Application No. 04737768.4, filed Jun. 3, 2004.

European Grant Notification dated May 27, 2009 in EP Application No. 04737768.4, filed Jun. 3, 2004.

* cited by examiner

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: aptamer of alpha thrombin

<400> SEQUENCE: 1
ggttggtgtg gttgg                                                    15

<210> SEQ ID NO 2
<211> LENGTH: 15
<212> TYPE: DNA
<213> ORGANISM: Artificial Sequence
<220> FEATURE:
<223> OTHER INFORMATION: artificial oligonucleotide
```

```
<400> SEQUENCE: 2
ggtggtggtt gtggt                                                15

<210> SEQ ID NO 3
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 3
attatacctg ggggagtatt gcggaggaag gtataat                        37
```

OPTICAL SENSORS BASED ON HYBRID APTAMER/CONJUGATED POLYMER COMPLEXES

This application is a national stage entry of PCT/CA04/00824 filed on Jun. 3, 2004, which claims priority from U.S. provisional application No. 60/474,950, filed on Jun. 3, 2003. This application claims the benefit of the prior-filed foreign application, CA 2430910, filed Jun. 3, 2003.

FIELD OF THE INVENTION

The present invention relates to optical sensors. More specifically, the present invention is concerned with optical sensors based on hybrid aptamer/conjugated polymer complexes.

BACKGROUND OF THE INVENTION

Intense research is being carried out worldwide with the goal of developing rapid, simple, specific, and sensitive detection tools for medical diagnostics and biomedical research applications. Fundamentally, most analytical tests and immunoassays rely on molecular recognition and its transduction into a measurable output. Among all the possible molecular recognition elements, artificial nucleic acid ligands (aptamers) have recently attracted a lot of interest due to their capability of binding various metal ions, amino acids, drugs, proteins, as well as other molecules having high affinity and specificity.[1-11]

Aptamers are usually isolated from combinatorial libraries of synthetic nucleic acids by an iterative process of adsorption, recovery, and amplification coined as SELEX (Systematic Evolution of Ligands by Exponential Procedure). Aptamer-based ligands constitute highly promising candidates for the specific detection of various molecules. Additionally, they can also be used in competition binding assays, such as for example in high-throughput screening assays[7], for the identification of new potential drugs capable of displacing the aptamers from their targets.

The above-mentioned approaches, however, require adequate transducing (i.e. reporting) elements in order to generate a physically measurable signal resulting from the recognition event. Binding of an aptamer to a target protein, for example, has been detected by using fluorescence (e.g. molecular beacons[12-13]) or by using a quartz microbalance[14]. In most cases, however, these methods either involve a tagging process or sophisticated experimental techniques. Furthermore, it is worth noting that labeling with various functional groups may even compromise the binding properties of the aptamers.

There thus remains a need to develop a rapid, simple, specific and sensitive detection tool capable of transducing the binding of an aptamer to its target into a clear signal.

The present invention seeks to meet these and other needs.

The present invention refers to a number of documents, the content of which is herein incorporated by reference in their entirety.

SUMMARY OF THE INVENTION

The present invention relates to optical sensors based on hybrid aptamer/conjugated polymer complexes. More specifically, the present invention relates to the use of a water-soluble cationic polythiophene derivative as a "polymeric stain" capable of specifically transducing the binding of an aptamer to its target into a clear optical (calorimetric or fluorometric) signal.

The present invention relates to an optical sensor for detecting a target comprising a single-stranded aptamer complementary to the target, and a water-soluble cationic polythiophene derivative of the following formula:

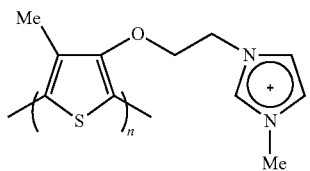

wherein "n" is an integer ranging from 6 to 100.

The present invention also relates to a method for detecting a target comprising the steps of:
a) contacting a sample suspected of containing the target with an optical sensor, the optical sensor including a single-stranded aptamer complementary to the target, and a water-soluble cationic polythiophene derivative of the following formula:

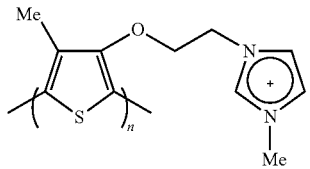

wherein "n" is an integer ranging from 6 to 100; and
b) detecting binding of the aptamer to the target by measuring an optical signal.

In addition, the present invention also relates to a method for detecting a target comprising the steps of:
a) contacting a sample suspected of containing the target with an aptamer known to be complementary to the target;
b) further contacting the sample with a water-soluble cationic polythiophene derivative of formula:

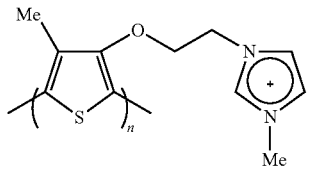

wherein "n" is an integer ranging from 6 to 100; and
c) detecting binding of the aptamer to the target by measuring an optical signal.

Furthermore, the present invention also relates to the use of an optical sensor comprising a single-stranded aptamer and a water-soluble cationic polythiophene derivative of the following formula:

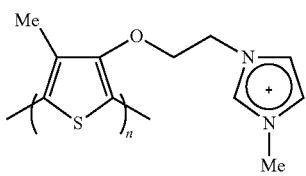

wherein "n" is an integer ranging from 6 to 100, for detecting a target, the aptamer being complementary to the target.

In a particular embodiment of the present invention, the target is human α-thrombin.

In a further particular embodiment of the present invention, the target is D-adenosine.

Further scope and applicability will become apparent from the detailed description given hereinafter. It should be understood however, that this detailed description, while indicating preferred embodiments of the invention, is given by way of illustration only, since various changes and modifications within the spirit and scope of the invention will become apparent to those skilled in the art.

BRIEF DESCRIPTION OF THE DRAWINGS

Having thus generally described the invention, reference will now be made to the accompanying drawings, showing by way of illustration preferred embodiments thereof, and in which.

Figure 1:
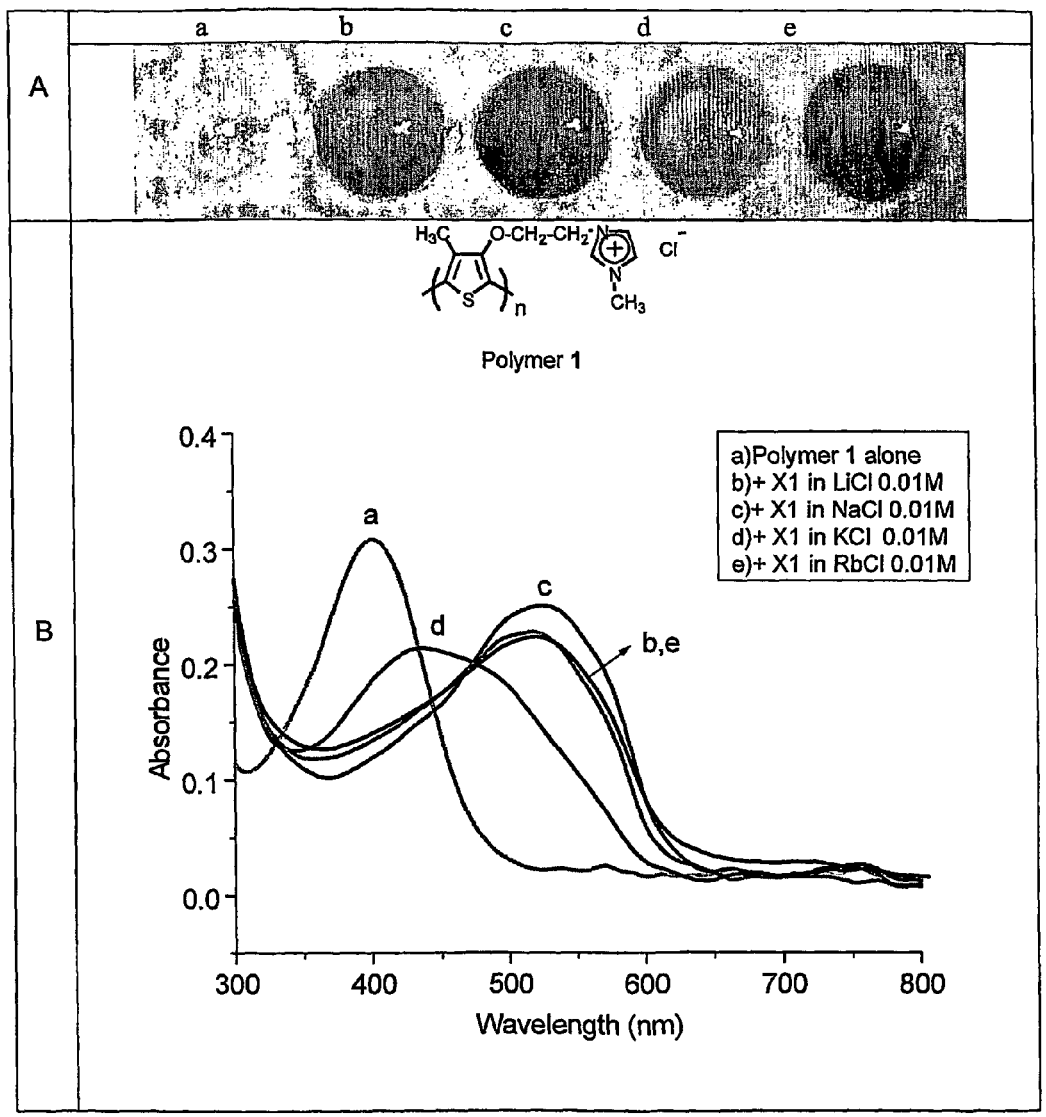
FIG. 1A shows photographs of polymer 1: (a) alone; (b) in the presence of X1 in LiCl 0.01M; (c) in the presence of X1 in NaCl 0.01M; (d) in the presence of X1 in KCl 0.01M; and (e) in the presence of X1 in RbCl 0.01M.
FIG. 1B shows the UV-Vis absorption spectra of polymer 1 ($2.9 \times 10^{-9}$ mole on a monomer unit basis) in the presence of X1 ($1.9 \times 10^{-10}$ mole of the 15-mer) and different salts in 100 μL of water at 25° C.

Other objects, advantages and features of the present invention will become more apparent upon reading of the following non-restrictive description, of preferred embodiments with reference to the accompanying drawings which is exemplary and should not be interpreted as limiting the scope of the present invention.

DETAILED DESCRIPTION OF SPECIFIC EMBODIMENTS

Unless defined otherwise, the scientific and technological terms and nomenclature used herein have the same meaning as commonly understood by a person of ordinary skill. Nevertheless, definitions of selected terms are provided for clarity and consistency.

As used herein, the term "optical sensor" is understood as referring to a complex consisting of a single-stranded aptamer and a water-soluble, cationic polythiophene derivative, the aptamer being complementary to a target to be detected, allowing for the detection of the target via optically measurable means. Without being so limited, these means include UV-visible or fluorescence spectra.

As used herein, the term "aptamer" is understood as being a single-stranded oligonucleotide that binds to a specific molecular target, non limiting examples of which are potassium ions, small organic molecules, amino acids, proteins, whole cells and nucleotides.

As used herein, when referring to an aptamer, the term "complementary" is understood as referring to the ability of the aptamer to hybridize with a specific chemical or biochemical target.

As used herein, the expression "enantiomeric resolution" is understood as referring to a discrimination (identification) between two enantiomers.

As used herein, the expression "folded structure" is understood as referring to a non-linear conformational structure.

As used herein, the term "target" is understood as referring to a charged entity, non-limiting examples of which are potassium ions, small organic molecules, amino acids, proteins, whole cells and nucleotides.

In a broad sense, the present invention relates to optical sensors based on hybrid aptamer/conjugated polymer complexes. More specifically, the present invention relates to the use of a water-soluble cationic polythiophene as a "polymeric stain" capable of specifically transducing the binding of an aptamer to its target into a clear optical (calorimetric or fluorometric) signal. The optical sensors do not require any chemical reaction to take place on the probes or with the analytes. Instead, the use of the optical sensors of the present invention is based on conformational changes as well as on electrostatic interactions between a cationic polythiophene derivative (i.e. poly(3-alkoxy-4-methylthiophene), an anionic single-stranded oligonucleotide (aptamer) and a target to be detected.

The present invention also relates to methods for detecting a charged entity using such optical sensors. Non-limiting examples of such charged entities include potassium ions, small organic molecules, amino acids, proteins, whole cells and nucleotides.

The use of the optical sensors of the present invention, for instance, allows to specifically detect as few as $2 \times 10^{-15}$ mol of human thrombin or $2 \times 10^{-14}$ mol of D-adenosine in only a few minutes and could be easily adapted for use in detecting many other chemical or biochemical targets non-limiting examples of which are ions, small organic molecules, amino acids, proteins, whole cells and nucleotides. Indeed, it is well known that the optical, electrical and electrochemical properties of polythiophenes are essentially constant after a minimum of 6-8 repeating units (P. Bäuerle, *The synthesis of Oligothiophenes*, Chapter 3 in Handbook of Oligo- and Polythiophenes, D. Fichou Ed., Wiley-VCH, Weinheim, pp. 89-181, 1999). A person skilled in the art would therefore understand that any polymer 1 having from 6 to 100 repeating units would work within an optical sensor as contemplated by the present invention. Furthermore, it is well known that aptamers with high affinity and selectivity have been created against a variety of targets, such as small organic molecules, peptides, proteins, and even cells (M. Famulok, G. Mayer, M Blind, *Acc. Chem. Res.* 33, 591-599, 2000). It is to be understood that any aptamer complementary to a target to be detected is within the scope of the present invention.

Single-stranded DNA (aptamer) can specifically bind potassium ions, human α-thrombin, or D-adenosine for instance. When binding takes place, the aptamer undergoes a conformational transition from an unfolded to a folded structure. This conformational change of the negatively-charged oligonucleotide can be detected by adding a water-soluble, cationic polythiophene derivative which transduces the new complex formation into an optical (calorimetric or fluorometric) signal without any labeling of the probe or of the target.

In a particular embodiment, an optical sensor according to the present invention comprises a polythiophene derivative, referred to herein as polymer 1, having the following formula:

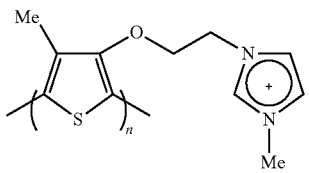

wherein "n" is an integer ranging from 6 to 100 (see FIG. 1).

The cationic, water-soluble, electroactive, and photoactive polymer 1 was prepared according to known literature procedures.[15] As is observed for most poly(3-alkoxy-4-methylthiophene)s,[16-19] polymer 1 exhibits chromic properties (color changes) which are due to conformational changes of the flexible conjugated backbone. Moreover, polymer 1 is known to display important optical changes when complexed to ss-DNA or ds-DNA[15], making it a good candidate for transducing the binding of an aptamer to a given target.

The monovalent potassium cation is known for its folding-inducing properties in several classes of nucleic acids.[20,21] As shown in FIG. 1, an aqueous solution of polymer 1 is yellow with a maximum absorption ($\lambda_{max}$) at 402 nm (FIG. 1A,a and B,a). This absorption maximum at a relatively short wavelength is related to a random-coil conformation of the polythiophene derivative, as any twisting of the conjugated backbone leads to a decrease of the effective conjugation length.[16]

Figure 2:
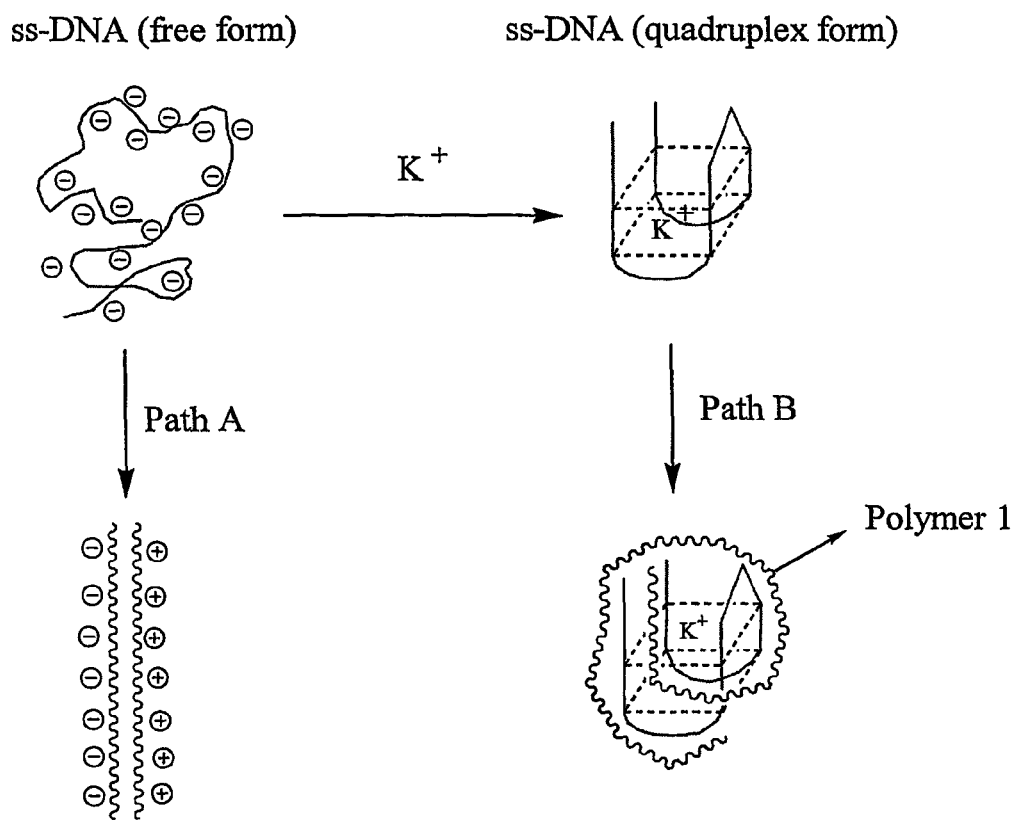
FIG. 2 shows the complexation between unfolded anionic ss-DNA and polymer 1 (Path A), as well as the complexation between unfolded anionic ss-DNA and polymer 1 in the presence of potassium ions (Path B)

A red color ($\lambda_{max}$=527 nm) was observed in the presence of LiCl (FIGS. 1A,b and B,b); NaCl (FIGS. 1A,c and B,c) or RbCl (FIGS. 1A,e and B,e) and ss-DNA (sequence X1: 5'-GGTTGGTGTGGTTGG-3' (SEQ, ID NO 1)). This red color shift is associated with a stoichiometric complexation between the unfolded anionic ss-DNA and the cationic polythiophene derivative (FIG. 2, path A). Such stoichiometric polyelectrolyte complexes tend to be insoluble in the medium in which they are formed and appear as aggregates.[15] These red-violet aggregates (probably formed from planar polymer chains) possess an absorption spectrum similar to that obtained in the solid state.

The optical properties (FIG. 1A,d and B,d), however, are different when potassium ions are present. As a result of the formation of a folded structure (quadruplex form) of oligonucleotide X1, stabilized by potassium ions ($K^+$), polymer 1 is able to wrap itself around this structure through electrostatic interactions (FIG. 2, Path B). Similar results were also observed when the chloride counter-ion was replaced by a bromide or iodide counter-anion, indicative of the specificity of the detection towards potassium cations.

In a particular embodiment of the present invention, human α-thrombin was selected as an example of a target to be detected since X1 ss-DNA sequence (5'-GGTTGGTGTGGT-TGG-3' (SEQ ID NO 1)) is known to be a specific binding sequence (i.e. an aptamer) of this protein. On the other hand, the oligonucleotide ss-DNA (X2: 5'-GGTGGTGGT-TGTGGT-3' (SEQ ID NO 2)) is known to be a non-binding sequence.[22] A conformational change occurs in the aptamer X1 when it binds to the thrombin molecule. Both NMR and X-ray diffraction studies have revealed that the aptamer adopts a compact unimolecular quadruplex structure with two G-quartets.[23, 24]

Figure 3:
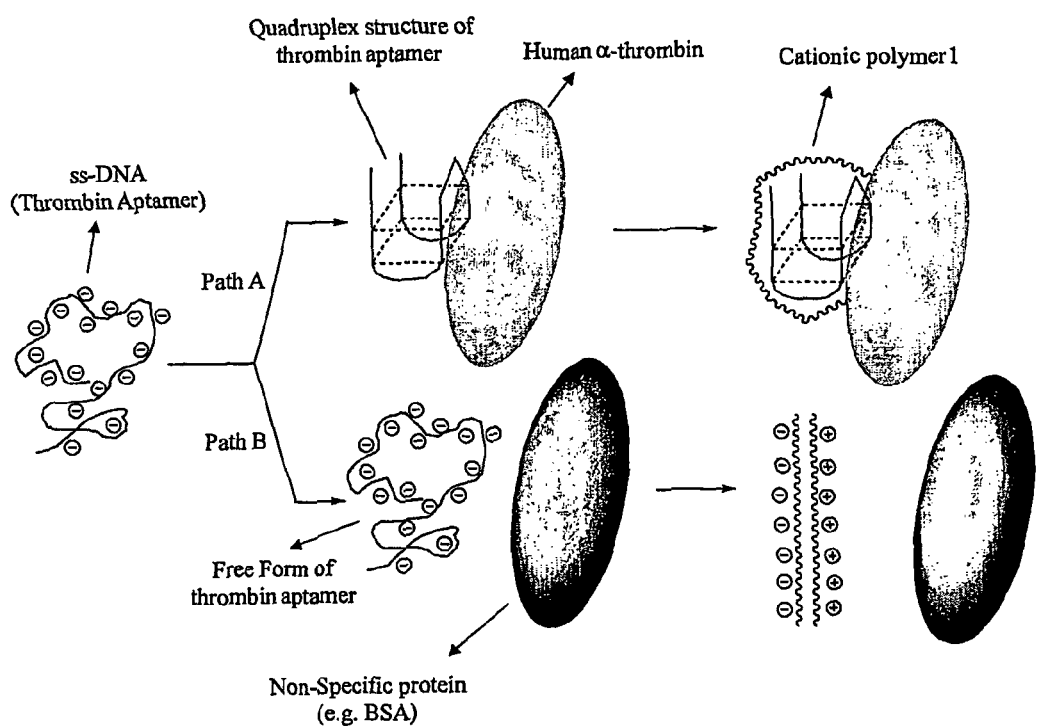
FIG. 3 illustrates the specific detection of human α-thrombin using ss-DNA thrombin aptamer X1 and positively-charged polymer 1.

As shown in FIG. 3, the specific detection of human α-thrombin is realized due to the formation of a quadruplex structure of the thrombin aptamer (X1). Accordingly, the 1:1:1 complex between polymer 1, X1, and α-thrombin has a similar orange color and UV-Visible absorption spectrum than that induced by $K^+$ (FIGS. 4b and 1B,d). Human α-thrombin promotes the formation of a folded structure (quadruplex form) of thrombin aptamer X1, enabling cationic polymer 1 to wrap itself around this quadruplex structure, which seems to partially hinder the aggregation and planarization of the polymer 1 when in the presence of ss-DNA X1 (FIG. 3, Path A). It is worth noting that only the stoechiometry of the aptamer (in terms of negative charges) and of polymer 1 (in terms of positive charges) has to be balanced, whereas an excess of α-thrombin does not influence its detection.

The specificity of the detection was verified by two control experiments carried out under identical conditions. In a first control experiment a non-binding sequence ss-DNA (X2: 5'-GGTGGTGGTTGTGGT-3' (SEQ ID NO 2)) was used (FIG. 4c) and in a second control experiment BSA (bovine serum albumin) was used (FIG. 4d). In both cases, an important red-shift toward lower energy ($\lambda_{max}$=505 nm) was observed. Furthermore, the color of these solutions was red-violet, which is typical of the planar and highly conjugated structure of the polythiophene backbone when mixed with unfolded ss-DNA (FIG. 3, Path B and FIG. 2, Path A). The detection limit of this colorimetric method is about $1 \times 10^{-11}$ mole of thrombin in a total volume of ca. 100 µL (a concentration of about $1 \times 10^{-7}$ M).

The fluorescent properties of conjugated polymers can also be utilized to detect very small quantities of analytes.[25-29] The fluorometric detection of the binding of the thrombin aptamer to human α-thrombin is possible because the fluorescence of poly(3-alkoxy-4-methylthiophene) is quenched in the planar, aggregated form.[15-19] The yellow, random-coil form of polymer 1 is fluorescent (FIG. 5a) with an emission maximum at 525 nm. When non-specific thrombin aptamer (X2) is used (FIG. 5c), or in the absence of human α-thrombin (FIG. 5d), the now red-violet, highly conjugated form has a much lower fluorescence intensity and the maximum of emission is red-shifted ($\lambda_{em}$=590 nm). However, when the 1:1:1 complex (human α-thrombin/thrombin aptamer X1/polymer 1) is formed (FIG. 5b), the resulting orange intermediate form is less fluorescent than the yellow form but more fluorescent (ca. a six-fold increase) than the red-violet form. This higher intensity of emission could be related to a partially planar conformation of the polythiophene chain, but with less aggregation of the chains.[30]

The use of a standard spectrofluorimeter provides for a detection limit of $2\times10^{-15}$ mole (a concentration of $1\times10^{-11}$ M in 200 μL) of human α-thrombin.

The resolution of small molecule enantiomers is of great importance in many research fields such as biochemistry and drug analysis. Two enantiomers of a same molecule may have distinct physiological behaviors; one enantiomeric form can be pharmaceutically active whereas the other enantiomeric form can be inactive or toxic.

In a further particular embodiment of the present invention, D-adenosine was selected as an example of a target to be detected.

More specifically, the enantiomeric resolution of D-adenosine and L-adenosine was performed using DNA aptamer (5'-ATTATACCTGGGGGAGTATTGCGGAG-GAAGGTATAAT-3' (SEQ ID NO 3)) (31).

In a first step, a framework composed of two stacked G-quartets is assumed by mixing D-adenosine and DNA aptamer (31) (5'-ATTATACCTGGGGGAGTATTGCGGAG-GAAGGTATAAT-3' (SEQ ID NO 3)). The formed complex is more stable at 5° C. The cationic polymer 1 is then added and is assumed to wrap itself around the previously formed complex. The stoichiometry of the adenosine enantiomer/aptamer/polymer 1 complex is 1:1 1.

A series of identical steps was then performed using L-adenosine. Since L-adenosine is not supposed to induce a conformational change in DNA aptamer (31) (5'-ATTATAC-CTGGGGGAGTATTGCGGAGGAAGGTATAAT-3' (SEQ ID NO 3)), the cationic polymer 1 should bind to the aptamer and lead to the formation of a duplex.

The cationic polymer 1 is yellow in aqueous solution (λ=397 nm) (FIG. 6a). Its maximum absorption is related to its random-coil conformation and is indicative of a decrease in the conjugation length. When L-adenosine is put in the presence of the aptamer (31) and polymer 1, a color change from yellow to red (λ=397 nm to λ=500 nm) (FIG. 6c) takes place. This reveals a planarization and aggregation of the polymer backbone through electrostatic interactions and an increase of the conjugation length. A partial return to its yellow form is observed (λ=410 nm with a shoulder at 510 nm) (FIG. 6b), when a complex is formed between the D-adenosine and aptamer (31), in presence of polymer 1. The detection limit by UV-visible absorption is about $1.8\times10^{-10}$ mole of D-adenosine in a total volume of ca. 200 μL (which gives a concentration of about $9\times10^{-7}$ M).

Since fluorescence spectroscopy is more sensitive than UV-visible absorption spectroscopy, the emission properties of polymer 1 can thus be used to detect even smaller quantities of D-adenosine. The yellow aqueous solution of polymer 1 is fluorescent with a maximum of emission at 525 nm (FIG. 7a). When L-adenosine is put in presence of aptamer 31 and polymer 1, the fluorescence of the red solution obtained is red-shifted and quenched (FIG. 7b). In the case of complexation between D-adenosine and aptamer 31 in presence of polymer 1, a partial recovery of the fluorescence could be observed (FIG. 7c). The detection limit using a standard spectrofluorimeter is about $1.8\times10^{-14}$ mole of D-adenosine in a total volume of ca. 200 μL (which gives a concentration of about $9\times10^{-11}$ M).

EXPERIMENTAL

UV-Visible Measurements

All UV-Visible absorption spectra were taken using a Hewlett-Packard (model 8452A) spectrophotometer.

Fluorescence Measurements

All fluorescence spectra were recorded on a Carry Eclipse (Varian Inc.) spectrofluorimeter. The excitation was performed at 420 nm.

EXAMPLE 1

Detection of Cations

In a quartz cell having an optical path length of 1.0 cm, 4 μL [$2.9\times10^{-9}$ mole (based on negative charges)] of 15-mer X1 were added to 100 μL of an aqueous solution of a given alkali metal cation (10 mM) (chloride salts), followed by the addition of 4 μL [$2.9\times10^{-9}$ mol (based on positive charge)] of a solution of cationic polymer 1. All UV-Visible absorption spectra were recorded at room temperature. The results are illustrated in FIG. 1.

EXAMPLE 2

Detection of Human α-Thrombin

In a UV quartz cell having an optical path length of 1.0 cm, $1.9\times10^{-10}$ mol of human α-thrombin (Haematologic Technologies Inc.) (the initial concentrated solution was diluted with sterilized water to obtain the appropriate concentration) and $2.9\times10^{-9}$ mol (based on negative charges or $1.9\times10^{-10}$ mol of 15-mer) of ss-DNA thrombin aptamer X1 were mixed in 100 μL of pure water at 25° C. This was followed by the addition of $2.9\times10^{-9}$ mol (based on charge repeat unit) of polymer 1, to form a complex (1/1/1).

Figure 4:
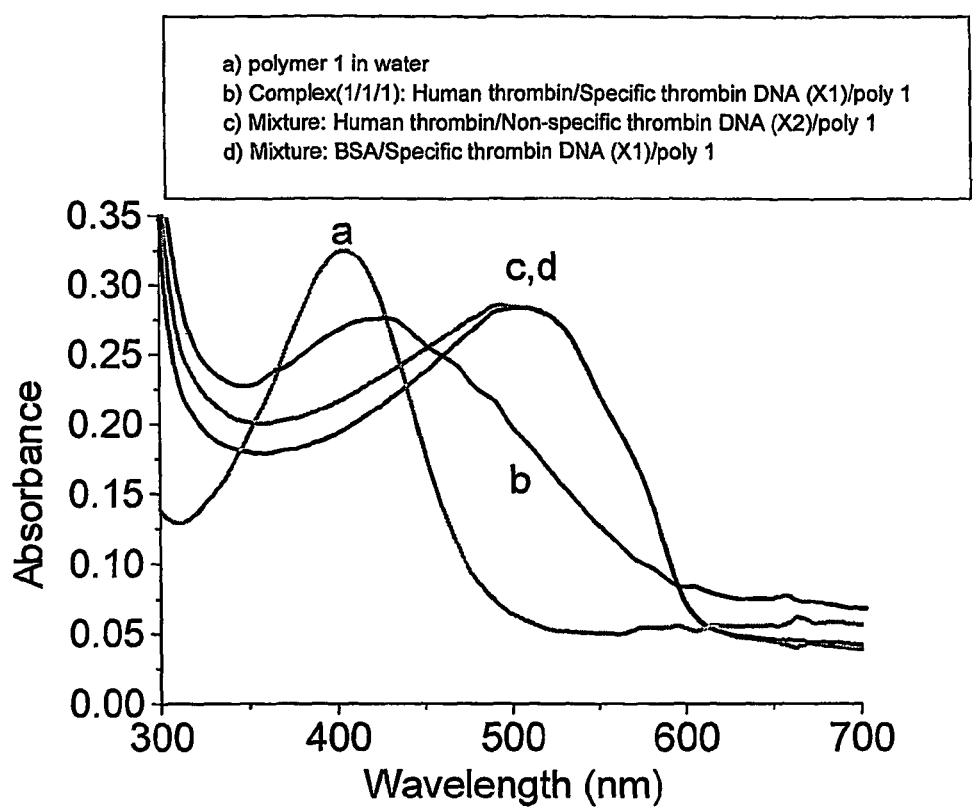
FIG. 4 illustrates the UV-Visible absorption spectrum of: (a) polymer 1 in water at 25° C.; (b) a complex (1/1/1) human thrombin/X1/polymer 1, in water at 25° C. (c) a mixture (1/1/1) of human thrombin/X2/polymer 1, in water at 25° C.; and (d) a mixture (1/1/1) of BSA/X1/polymer 1, in water at 25° C.

Two control experiments were carried out using a non-specific sequence X2 and BSA (bovine serum albumin, obtained from Sigma), under identical conditions. The results are illustrated in FIG. 4.

EXAMPLE 3

Detection of D-Adenosine

In a UV quartz cell having an optical path length of 1.0 cm, $2.9\times10^{-9}$ mol of D-adenosine and $1.08\times10^{-7}$ mol of DNA D-adenosine aptamer (based on monomeric negative charges or $2.9\times10^{-9}$ mol of 37-mers) were mixed in 200 μL of pure water at 5° C. This was followed by the addition of $1.08\times10^{-7}$ mol (based on charge repeat unit) of polymer 1, to form a complex (1/1/1).

Figure 6:
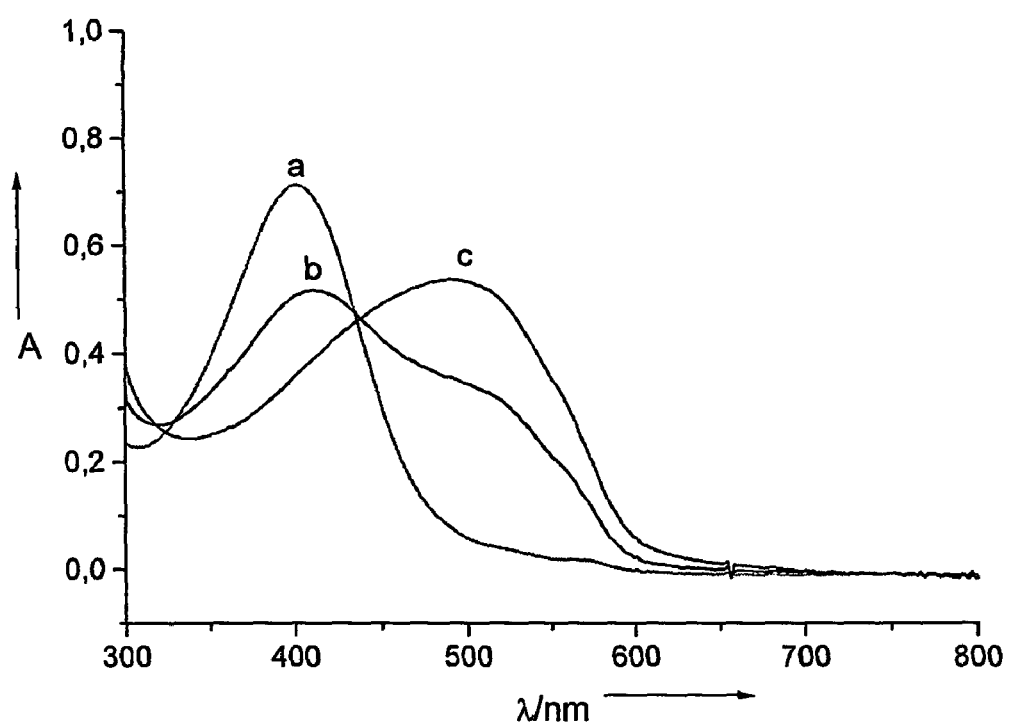
FIG. 6 illustrates the UV-visible spectrum of: (a) $1.08 \times 10^{-7}$ mol of cationic polymer 1 in 200 μl of water at 5° C.; (b) a mixture of $2.9 \times 10^{-9}$ mol of D-adenosine, $1.08 \times 10^{-7}$ mol of DNA D-adenosine aptamer (based on monomeric negative charge or $2.9 \times 10^{-9}$ mol of 37-mers) and $1.08 \times 10^{-7}$ (based on charge unit) of polymer 1 in 200 μl of water at 5° C.; and (c) a mixture of $2.9 \times 10^{-9}$ mol of L-adenosine, $1.08 \times 10^{-7}$ mol of DNA D-adenosine aptamer (based on monomeric negative charge or $2.9 \times 10^{-9}$ mol of 37-mers) and $1.08 \times 10^{-7}$ (based on charge unit) of polymer 1 in 200 μl of water at 5° C.

A control experiment, under identical conditions, was carried out using L-adenosine, to which the D-adenosine aptamer is not complementary. The results are illustrated in FIG. 6.

EXAMPLE 4

Detection of Human α-Thrombin

In a fluorescence cell having an optical path length of 3.0 mm, $3.8\times10^{-10}$ mol of human α-thrombin and $5.7\times10^{-9}$ mole (based on monomeric negative charge or $3.8\times10^{-10}$ mol of 15-mer) of ss-DNA thrombin aptamer X1 were mixed in 200 μl of pure water, followed by the addition of $5.7\times10^{-9}$ mol (based on charge repeat unit) of polymer 1. The fluorescence spectrum of all mixtures was recorded at 5° C. For the lower concentration of human α-thrombin, the excitation was performed at, 420 nm, and the fluorescence emission intensity was measured at 584 nm (without recording the entire emission spectrum).

Figure 5:
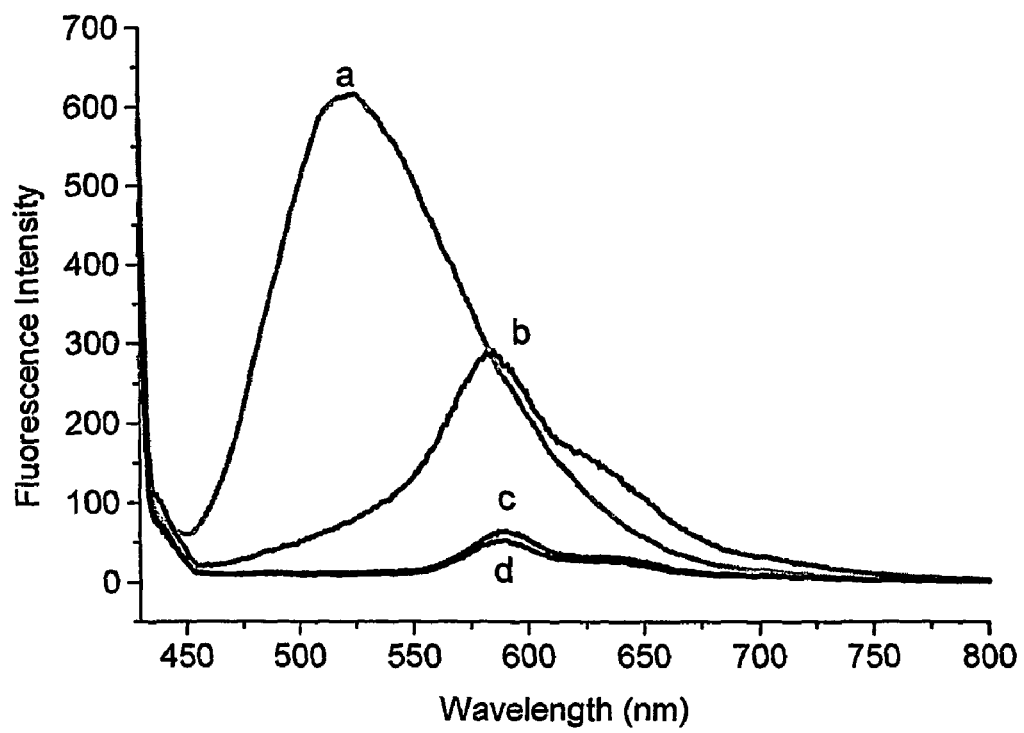
FIG. 5 illustrates the fluorescence spectrum measured at 5° C. of: (a) polymer 1; (b) human thrombin/X1/polymer 1 complex (1/1/1); (c) human thrombin/X2/polymer 1 mixture (1/1/1); and (d) X1/polymer 1 complex (1/1) in water.

A control experiment was carried out using a non-specific sequence X2 under identical conditions. The results are illustrated in FIG. 5.

EXAMPLE 5

Detection of D-Adenosine

Figure 7:
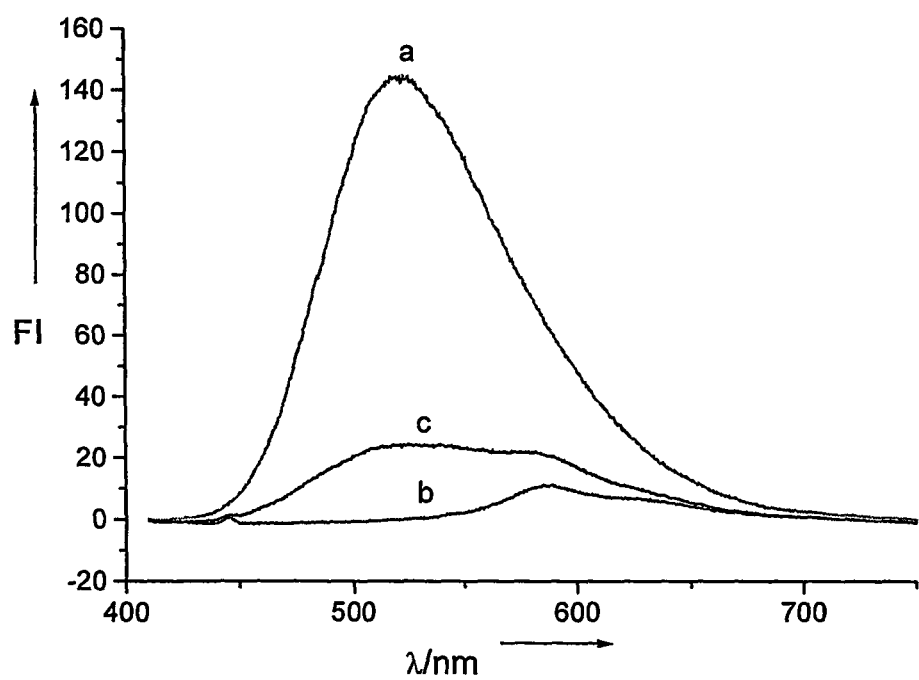
FIG. 7 illustrates the emission spectrum of: (a) $1.08 \times 10^{-7}$ mol of cationic polymer 1 in 200 μl of water at 5° C.; (b) a mixture of $2.9 \times 10^{-9}$ mol of D-adenosine, $1.08 \times 10^{-7}$ mol of DNA D-adenosine aptamer (based on monomeric negative charge or $2.9 \times 10^{-9}$ mol of 37-mers) and $1.08 \times 10^{-7}$ (based on charge unit) of polymer 1 in 200 μl of water at 5° C.; (c) a mixture of $2.9 \times 10^{-9}$ mol of L-adenosine, $1.08 \times 10^{-7}$ mol of DNA D-adenosine aptamer (based on monomeric negative charge or $2.9 \times 10^{-9}$ mol of 37-mers) and $1.08 \times 10^{-7}$ (based on charge unit) of polymer 1 in 200 μl of water at 5° C.

In a fluorescence cell having an optical path length of 3.0 mm, $2.9 \times 10^{-9}$ mol of D-adenosine and $1.08 \times 10^{-7}$ mol of DNA D-adenosine aptamer (based on monomeric negative charge or $2.9 \times 10^{-9}$ mol of 37-mers) were mixed in 200 μl of pure water, followed by the addition of $1.08 \times 10^{-7}$ mol (based on charge repeat unit) of polymer 1. The fluorescence spectrum of all mixtures was recorded at 5° C. The results are illustrated in FIG. 7.

A control experiment, under identical conditions, was carried out using L-adenosine, to which the D-adenosine aptamer is not complementary. The results are illustrated in FIG. 7.

Although the present invention has been described hereinabove by way of preferred embodiments thereof, it can be modified, without departing from the spirit and nature of the subject invention as defined in the appended claims.

REFERENCES

1. M. P. Robertson, G. F. Joyce, *Nature* 344, 467 (1990).
2. A. D. Ellington, J. W. Szostak; *Nature* 346, 818 (1990).
3. C. Tuerk, L. Gold, *Science* 249, 505 (1990).
4. C. K. O'Sullivan, *Anal. Bioanal. Chem.* 372, 44 (2002).
5. S. L. Clark, V. T. Remcho, *Electrophoresis* 23, 1335 (2002).
6. D. W. Drolet, L. M. McDermott, T. S. Romig, *Nature Biotechnol.* 14, 1021 (1996).
7. L. S. Green, C. Bell, N. Janjic, *Biotechniques* 30, 1094 (2001).
8. K. A. Davis, B. Abrams, Y. Lin, S. D. Jayasena, *Nucleic Acids Res* 24, 702 (1996).
9. Y. Lin, D. Nieulandt, A. Magallanez, B. Feistner, S. D. Jayasena, *Nucleic Acids Res.* 24, 3407 (1996).
10. M. Blank, T. Weinschenk, M. Priemer, H. Schluesener, *J. Biol. Chem.* 276, 16464 (2001).
11. M. Lee, D. R. Walt, *Anal. Biochem.* 282, 142 (2000).
12. N. Hamaguchi, A. Ellington, M. Stanton, *Anal. Biochem.* 294, 126 (2001).
13. J. L. Jianwei, F. Xiaohong, T. Weihong, *Biochem. Biophys. Res. Commun.* 292, 31 (2002).
14. M. Liss, B. Petersen, H. Wolf, E. Prohaska, *Anal. Chem.* 74, 4488 (2002).
15. H. A. Ho, M. Boissinot, M. G. Bergeron, G. Corbeil, K. Doré, D. Boudreau, M. Leclerc, *Angew. Chem. Int. Ed.* 41, 1548 (2002).
16. M. Leclerc, *Adv. Mater.* 11, 1491 (1999).
17. K. Faïd, M. Leclerc, *J. Am. Chem. Soc.* 120, 5274 (1998).
18. S. Bernier, S. Garreau, M. Béra-Abérem, C. Gravel, M. Leclerc, *J. Am. Chem. Soc,* 124, 12463 (2002).
19. H. A. Ho, M. Leclerc, *J. Am. Chem. Soc.* 125, 4412 (2003).
20. S. Basu, A. A. Szewczak, M. Cocco, S. A. Strobel. *J. Am. Chem. Soc.* 122, 3240 (2000).
21. H. Ueyama, M. Takagi, S. Takenaka, *J. Am. Chem. Soc.* 124, 14286 (2002).
22. L. C. Bock, L. C. Griffin, J. A. Latham, E. H. Vermaas, J. J. Toole, *Nature* 355, 564 (1992).
23. K. Y. Wang, S. McCurdy, R. G. Shea, S. Swaminathan, P. H. Bolton, *Biochemistry,* 32, 1899 (1993).
24. K. Padmanabhan, K. P. Padmanablan, J. D. Ferrara, J. E. Sadler, A. Tulinsky, *J. Biol. Chem.,* 268, 17651 (1993).
25. D. T. McQuade, A. E. Pullen, T. M. Swager, *Chem. Rev.* 100, 2537 (2000).
26. L. Chen, D. W. McBranch, H. L. Wang, R. Hegelson, F. Wudl, D. G. Whitten, *Proc. Natl. Acad. Sci. U.S.A.* 96, 12287 (1999).
27. C. Fan, K. W. Plaxco, A. J. Heeger, *J. Am. Chem. Soc.* 124, 5642 (2002).
28. B. S. Gaylord, A. J. Heeger, G. C. Bazan, *J. Am. Chem. Soc.* 125, 896 (2003).
29. C. Fan, T. Hirasa, K. W. Plaxco, A. J. Heeger, *Langmuir* 19, 3554 (2003).
30. K. P. R. Nilsson, M. R. Andersson, O. Inganäs, *J. Phys. Condens. Matter* 14, 10011 (2002).
31. M. Michaud, E. Jourdan, C. Ravelet, A. Villet, A. Ravel, C. Grosset, E. Peyrin, *Anal. Chem.* 76, 1015 (2004).

---

The invention claimed is:

1. An optical sensor for detecting a quadruplex G-quartet structure of a target bound by a single stranded aptamer complementary to said target, the optical sensor comprising:
   the single-stranded aptamer complementary to said target, wherein said aptamer and target complex form the quadruplex G-quartet structure; and
   a water-soluble cationic polythiophene derivative of the following formula:

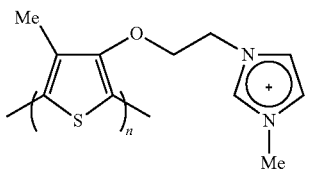

wherein "n" is an integer ranging from 6 to 100, and
wherein the said target is selected from the group consisting of potassium ions, small organic molecules, amino acids, proteins, whole cells and nucleotides.

2. The optical sensor of claim 1, wherein said aptamer is single-stranded DNA.

3. The optical sensor of claim 2, wherein said single-stranded DNA has the following sequence:

(SEQ ID NO 1)
5'-GGTTGGTGTGGTTGG-3'.

4. The optical sensor of claim 3, wherein said target is human α-thrombin.

5. The optical sensor of claim 2, wherein said single-stranded DNA has the following sequence:

(SEQ ID NO 3)
5'-ATTATACCTGGGGGAGTATTGCGGAGGAAGGTATAAT-3'.

6. The optical sensor of claim 5, wherein said target is D-adenosine.

7. A method for detecting a quadruplex G-quartet structure of a target bound by a single stranded aptamer complementary to said target comprising the steps of:
   a) contacting a sample suspected of containing the target with an optical sensor, said optical sensor comprising:
      the single-stranded aptamer complementary to said target, wherein said aptamer complexes with the target to form the quadruplex G-quartet structure; and
      a water soluble cationic polythiophene derivative of the following formula:

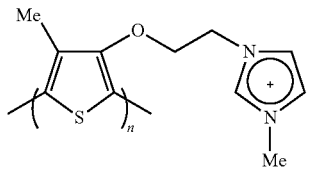

wherein "n" is an integer ranging from 6 to 100; and
   b) detecting binding of the aptamer to the target by detecting whether the quadruplex G-quartet structure has been formed by measuring an optical signal.

8. The method of claim 7, wherein said optical signal is a UV-Visible absorption or fluorescence spectrum.

9. The method of claim 8, wherein said target is selected from the group consisting of potassium ions, small organic molecules, amino acids, proteins, whole cells and nucleotides.

10. The method of claim 8, wherein said aptamer is an oligonucleotide.

11. The method of claim 10, wherein said oligonucleotide is single-stranded DNA.

12. The method of claim 11, wherein said single-stranded DNA has the following sequence:

(SEQ ID NO 1)
5'-GGTTGGTGTGGTTGG-3'.

13. The method of claim 12, wherein said target is human α-thrombin.

14. The method of claim 11, wherein said single-stranded DNA has the following sequence:

(SEQ ID NO 3)
5'-ATTATACCTGGGGGAGTATTGCGGAGGAAGGTATAAT-3'.

15. The method of claim 14, wherein said target is D-adenosine.

16. A method for detecting a quadruplex G-quartet structure of a target bound by a single stranded aptamer complementary to said target comprising the steps of:
   a) contacting a sample suspected of containing the target with said single stranded aptamer complementary to the target;

b) further contacting the sample with a water-soluble cationic polythiophene derivative of formula:

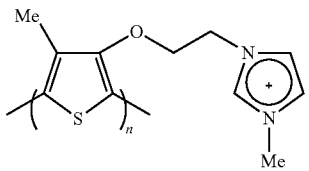

wherein "n" is an integer ranging from 6 to 100; and
c) detecting binding of the aptamer to the target by detecting whether the quadruplex G-quartet structure has been formed by measuring an optical signal.

17. The method of claim 16, wherein said optical signal is a UV-Visible absorption or fluorescence spectrum.

18. The method of claim 17, wherein said target is selected from the group consisting of potassium ions, small organic molecules, amino acids, proteins, whole cells and nucleotides.

19. The method of claim 17, wherein said aptamer is an oligonucleotide.

20. The method of claim 19, wherein said oligonucleotide is single-stranded DNA.

21. The method of claim 20, wherein said single-stranded DNA has the following sequence:

```
                                              (SEQ ID NO 1)
      5'-GGTTGGTGTGGTTGG-3'.
```

22. The method of claim 21, wherein said target is human α-thrombin.

23. The method of claim 20, wherein said single-stranded DNA has the following sequence:

```
                                              (SEQ ID NO 3)
      5'-ATTATACCTGGGGGAGTATTGCGGAGGAAGGTATAAT-3'.
```

24. The method of claim 23, wherein said target is D-adenosine.

25. The method of claim 13, wherein said human α-thrombin is present in an amount of at least $1\times10^{-7}$ molar.

26. The method of claim 15, wherein said D-adenosine is present in an amount of at least $9\times10^{-11}$ molar.

* * * * *

UNITED STATES PATENT AND TRADEMARK OFFICE
CERTIFICATE OF CORRECTION

PATENT NO.         : 8,409,797 B2
APPLICATION NO.    : 10/559098
DATED              : April 2, 2013
INVENTOR(S)        : Leclerc et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1034 days.

Signed and Sealed this
First Day of September, 2015

Michelle K. Lee
*Director of the United States Patent and Trademark Office*